United States Patent [19]

Lu

[11] Patent Number: 5,268,087

[45] Date of Patent: Dec. 7, 1993

[54] ELECTROPLATING TEST CELL

[75] Inventor: Po-Yen Lu, Westfield, N.J.

[73] Assignee: AT&T Bell Laboratories, Murray Hill, N.J.

[21] Appl. No.: 814,309

[22] Filed: Dec. 23, 1991

Related U.S. Application Data

[63] Continuation of Ser. No. 549,855, Jul. 9, 1990, abandoned.

[51] Int. Cl.$^5$ ............................................. G01N 27/42
[52] U.S. Cl. .................................................... 204/434
[58] Field of Search ...................... 204/153.1, 212, 434

[56] References Cited

U.S. PATENT DOCUMENTS

| | | | |
|---|---|---|---|
| 2,149,344 | 3/1939 | Hull | 204/1 |
| 2,760,928 | 8/1956 | Ceresa | 204/195 |
| 2,801,963 | 8/1957 | Hull et al. | 204/195 |
| 3,121,053 | 2/1964 | Hull, Jr. et al. | 204/195 |
| 3,215,609 | 11/1965 | Chapdelaine | 204/434 X |
| 3,223,598 | 12/1965 | Jacky et al. | 204/434 X |
| 4,102,770 | 7/1978 | Moriarty et al. | 204/434 |
| 4,252,027 | 2/1981 | Ogden et al. | 73/826 |
| 4,487,681 | 12/1984 | Cordes | 204/434 |

OTHER PUBLICATIONS

Afshar, et al, "Rotating Electrode Current Density Cells to Simulate High Speed Electrodeposition", *Transactions of the Institute of Metal Finishing*, vol. 69, part 1, pp. 37-44, Feb. 1991.

*Transactions of the Institute of Metal Finishing*, vol. 68, part 1, p. 2.

Patent Abstracts of Japan, vol. 10, No. 271 (P-497) [2327], Sep. 16, 1986 & JP-A-61 95 242 (Toyota Motor Corp.) May 14, 1986.

R. O. Hull, "Current Density Range Characteristics—Their Determination and Application", Proc. Amer. Electroplaters Society, 27 (1939), pp. 52-60.

J. S. Newman, Electrochemical Systems, Prentice-Hall, Inc., Englewood, Cliffs, N.J. (1973), pp. 2-9, 307-309.

Chin-Sheug Wu, "The Three Dimensional Incompressible Laminar Boundary Layer on a Spinning Cone", Appl. Sci. Res., Section A, vol. 8 (1959), pp. 140-146.

C. L. Tien, "Heat Transfer By Laminar Flow From a Rotating Cone", Journal of Heat Transfer, C 82 (1960), pp. 252-253.

J. Newman, "Schmidt Number Correction For The Rotating Disc", The Journal of Physical Chemistry, vol. 70, No. 7, Apr. 1966, pp. 1327-1328.

Dr. Hermann Schlichting, "Boundary-Layer Theory", Sixth Ed., McGraw-Hill Book Company (1968), p. 93.

A. J. Arvia, et al, "Mass Transfer in the Electrolysis . . . ", Electrochimica Acta, 1962, vol. 7, pp. 65-78, Pergamon Press, Ltd.

*Primary Examiner*—Nam Nguyen
*Attorney, Agent, or Firm*—Oleg E. Alber

[57] ABSTRACT

Hull cell has been widely used in the plating industry for many years to evaluate the plating chemistry as a function of current densities. However, because of irreproducible mass transfer, Hull cells can only be used qualitatively for process control. A new design of an improved cell with extremely reproducible mass transfer performance utilizes a rotatable cathode, and permits quantitative analysis of the performance of the cell. The improved cell can also be used to study the mass transfer effect on deposit properties and throwing power, which can not be provided by the traditional Hull cell.

6 Claims, 3 Drawing Sheets

ELECTROPLATING TEST CELL

This application is a continuation of application Ser. No. 07/549855, filed on Jul. 9, 1990, abandoned.

TECHNICAL FIELD

This invention concerns with an improved electroplating test cell useful for evaluating and studying electrodeposition.

BACKGROUND OF THE INVENTION

Advances in analytical techniques make it feasible to accurately determine the concentration of most metal ions and salts in a plating solution. However, the analysis of organic plating additives (typically in the ppm level), contaminants from drag-in, and plating reaction by-products, is usually very difficult, if not impossible. Even when "complete" analysis is possible for a plating solution, there is always a concern about "unknown species" that may affect the plated deposit. In practice, in addition to the analytical technique, other methods are used for routine checking of the overall performance of plating solutions.

Hull cell has been recognized as one of the most important tools to monitor overall performance of plating solutions. Hull cell was first described by R. O. Hull in a paper entitled "Current Density Range Characteristics, Their Determination and Application", Proc. Amer. Electroplates' Soc., 27 (1939) pp. 52–60. Also see U.S. Pat. No. 2,149,344 issued on Mar. 7, 1939 to R. O. Hull. One of the principle advantages of Hull cell measurements is that it is possible to assess the deposit characteristics at various current densities on a single test panel. It is also possible to carry out evaluations using various temperatures, solution compositions, addition agents, contaminants, etc.

Essentially, a Hull cell is an electro-plating cell with a particular trapezoidal geometry (FIG. 6). A flat cathode, 61, is fixed at an angle to a flat anode, 62, within a box-like container, 63, holding an electrolyte, 64. Both the cathode and the anode occupy the full cross-section of the cell. Several sizes of Hull cells are commercially available with solution capacities of 250, 267, 320, 534 and 1000 cc. The principle behind the Hull cell is to create a variation of solution resistance between the electrodes and to use a current restricting angle between the cathode and an insulating plane. The above arrangement produces a large variation of current density across the deposition on the test panel. Agitation within the Hull cell is usually provided by an external paddle, magnetic stirring bar or by forcing air through the electrolyte in the vicinity of the cathode. However, the results are usually less meaningful due to poorly reproducible mass transfer characteristic between experimental runs. Electrochemical reaction kinetics are usually greatly influenced by trace amounts of organic-/inorganic additives and the concentration of metal ions and salts. Therefore, different degrees of agitation near the plating object will result in large variations in deposit properties. Unfortunately, the traditional Hull cell does not provide a reproducible mass transfer and, therefore, can only be used for qualitative process control.

The intention of a Hull cell is to create large variations of current density over the test panel, typically over one order of magnitude. It is conceivable that at the high current density region, the plating reaction is mass transfer limited or nearly mass transfer limited. A deposit obtained from a mass transfer limited condition has a different structure when compared to a deposit plated at conditions that are not mass transfer limited. Therefore, it is difficult to determine whether an irregular deposit is the result of a change of plating variables or is simply caused by irreproducible mass transfer.

Thus, there is a need for a new design of a cell which permits assessment of deposit characteristics at various current densities on a single test panel and which also has reproducible mass transfer and could be useful for quantitative measurements.

SUMMARY OF THE INVENTION

This invention is an electroplating test cell comprising a container for holding a desired volume of an electrolyte, an anode, a cathode positioned coaxially of the container and of the anode, and a current density variation creating (cdvc) means of an electrically insulating material for creating, for a given total current, a current density variation across the cathode, said cdvc means being arranged at an angle of less than 90 degrees to that surface of the cathode on which metal deposition is to take place. The cathode is fully immersed in the electrolyte and is capable of being rotated about its central axis over a high range of RPMs. This design of the test cell leads to reproducible mass transfer performance and permits not only a qualitative but also a quantitative analysis for the performance of the cell, which cannot be effectively provided by the traditional Hull cell.

DETAILED DESCRIPTION

Figure 1:
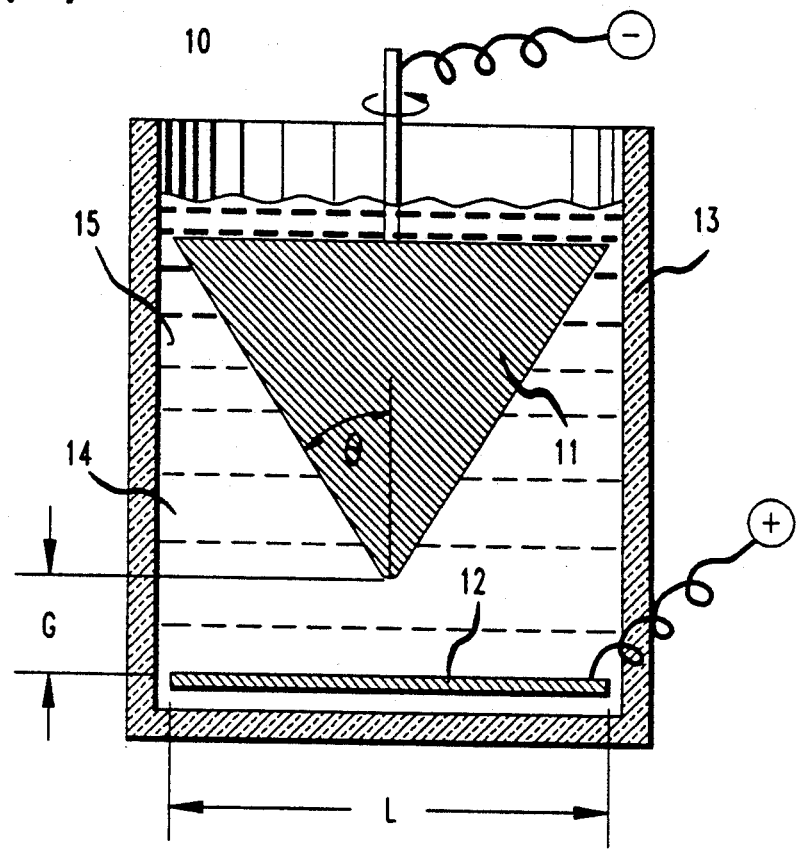
FIG. 1 is a schematic representation of a cell with a rotating cone cathode and a stationary disk anode.

This invention is an improved electroplating test cell useful for evaluating and studying electrodeposition. The basis of an improved electroplating cell is the combination of the current density variation feature of a Hull cell with the reproducible mass transfer feature of a rotating electrode. The cell design consists of a cathode capable of being rotated about its central axis, an anode (either stationary or rotatable), and current restricting shield (forming a less than 90 degree angle with the cathode). The cell comprises a container of non-conducting, non-contaminating insulating material for holding a predetermined amount of an electrolyte, an anode and a cathode which are submersed in the electrolyte, and a current density variation creating (cdvc) means.

The container is of an insulating material, such as glass, glazed ceramic, plastic materials such as polyethylene, polyprophylene, polyvinyl chloride, teflon and others. The size of the container is selected such that when a predetermined amount of electrolyte, e.g. 250, 500 or 1,000 ml, is in the container, the anode and the cathode are covered completely by the electrolyte. The electrode closest to the surface of the electrolyte, e.g. a base of cone 11 in FIG. 1, should be covered completely by a thin layer of electrolyte kept to a minimum, e.g. less than 5 mm in thickness. Layer thickness which could contribute to an unwanted "edge effect" (which takes primary current, e.g. 2A, to infinity) due to current flow in the electrolyte layer, should be avoided. Preferably, the container has a cylindrical shape, but other configurations, e.g. polygonal shape, are possible with an anode having a cylindrical shape or even with an insulating cylinder or truncated cone insert placed coaxially of the container between the walls of the container and the rotating cathode. Polygonal shape without a cylindrical insert is unwanted due to the unsymmetrical nature for current distribution in the angular direction.

The anode may have various configurations including such configurations as a disc, an annulus, a cylinder. The cathode also may have various configurations including such as a disk, a cone and a cylinder. The cathode which is rotatable about its central axis, is suspended in the container, preferably coaxially of the longitudinal axis of the container. The cathode is suspended by means of a support arm (not shown) which also includes variable drive means (not shown) to provide for rotation of the cathode about its central axis. The cathode has typically a polished metal surface, with such metals as copper, brass or stainless steel being preferred. A surface of the cathode facing toward the surface of the electrolyte may be provided with an insulating material to avoid the possibility of unwanted deposition on that surface.

To permit repeated use of the cathode, a removable test panel may be placed over the plating surface of the cathode for each test. The panel should conform to the plating surface, and be of a metal suitable for plating thereon, with such metals as copper, brass or stainless steel being preferred. The longitudinal dimensions are preselected in a ratio which approximates that of a Hull cell with a corresponding volume of electrolyte.

Regarding the mass transfer aspect, rotating electrodes (including disk, cone, cylinder shape) are among the few convective flow systems for which the hydrodynamic equations and the convective-diffusion equations have been rigorously solved and experimentally confirmed, for example, see C. L. Tien, "Heat Transfer by Laminar Flow From a Rotating Cone", Journal of Heat Transfer, August, 1960, pp. 252-253, and Dr. Hermann Schlichting, "Boundary-Layer Theory", McGraw-Hill Book Company, New York (1968), p. 93. In a typical plating solution, because of the large Schmidt number($v/D$), the mass transfer boundary layer is much thinner than the hydrodynamic boundary layer, e.g. see, John Newman, "Electrochemical Systems", Prentice-Hall, Inc., New Jersey (1973), p. 307. Therefore, the mass transfer characteristics of a rotating electrode are well defined. The superior mass transfer reproducibility enables these rotating electrodes to be used in measuring fundamental constants such as diffusion coefficients and electrochemical reaction kinetic constants.

Based on the above principle, many versions of the improved cells may be designed. Below are described, four different exemplary versions of this cell. Undoubtedly, some other versions of the improved cell using the rotating symmetrical cathode principle can be easily reconstructed on the basis of the within teachings.

One embodiment of the improved cell, 10, is schematically represented in FIG. 1 in which a cathode, 11, and an anode, 12, are positioned in a container, 13, of a suitable non-conducting, non-contaminating material holding a preselected volume of an electrolyte, 14. In this embodiment, cathode 11 is a cone-shaped electrode which is capable of being rotated about its central axis and anode 12 is a stationary disk, with the wall 15 of the container acting as a cdvc means. Current density at the cathode varies from a high at the apex of the cone (nearest to the anode) to a low farthest from the anode. Variation of the current density along the surface of the cone can be further adjusted by adjusting at least one of the gap (G) between the tip of the cone and the anode, the diameter of the anode (L) and the angle ($\Theta$) between the cone surface and the central axis of the cone. Current density at the cathode varies from a high at the apex of the cone (nearest to the anode to a low farthest from the anode.

Figure 2:
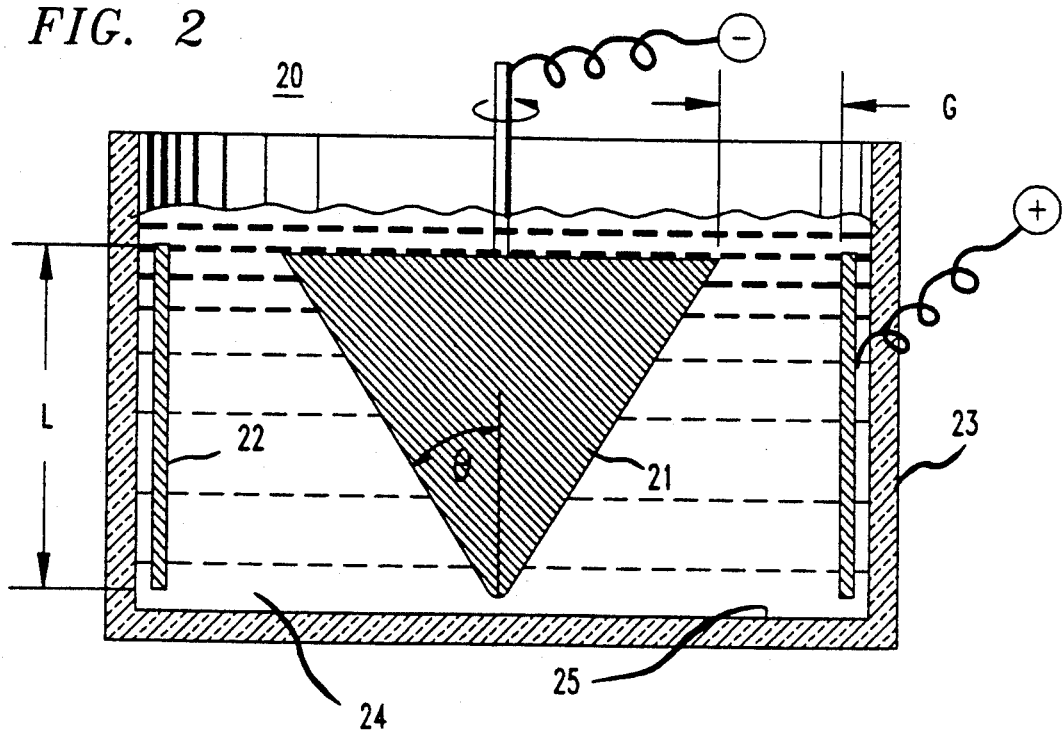
FIG. 2 is a schematic representation of a cell with a rotating cone cathode and a stationary cylinder anode.

Another embodiment of the improved cell, denominated as 20, is schematically represented in FIG. 2 in which a cathode 21 and an anode 22 are positioned in a container, 23, of suitable non-conducting, non-contaminating material, holding a preselected volume of an electrolyte, 24. Cathode 21 is a rotatable cone, while anode 22 is a stationary cylinder encompassing the cathode, with the bottom, 25, of container 23 acting as a cdvc means. Current density at the cathode varies from a high at the base of the cone (nearest the anode) to a low at the apex of the cone. Variation of the current density can be further obtained by varying at least one of a gap (G) between the edge of the cone and the anode, the width of the anode (L) and the angle ($\Theta$) between the cone surface and the central axis of the cone.

Figure 3:
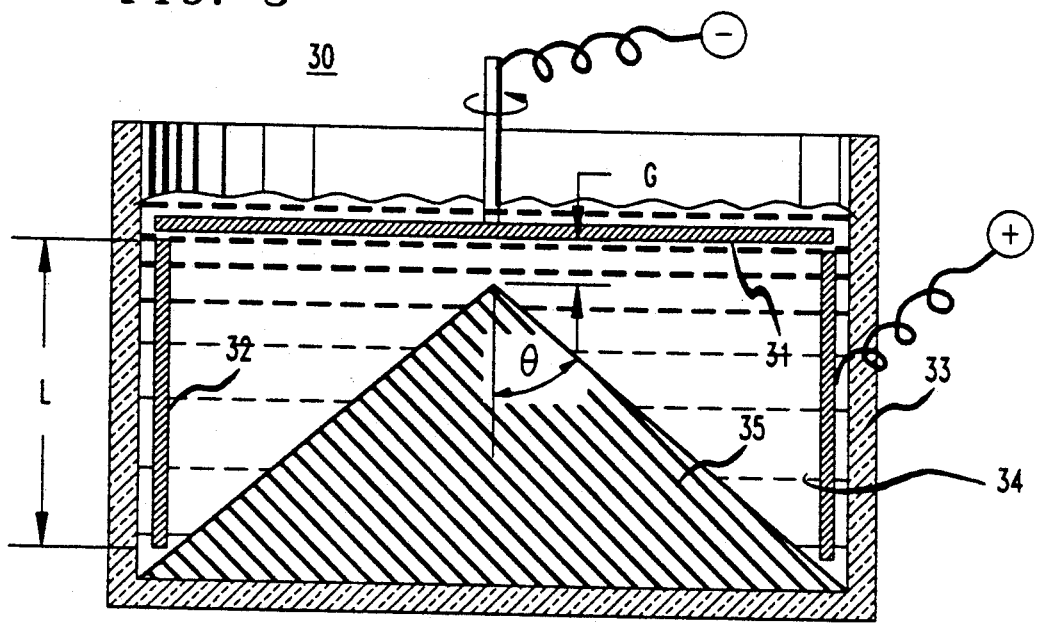
FIG. 3 is a schematic representation of a cell with a rotating disk cathode and a stationary cylinder anode.

A further embodiment of the improved cell, denominated 30, is schematically represented in FIG. 3 in which a cathode, 31, and an anode, 32, are positioned in a container, 33, of suitable non-conducting, non-contaminating material, holding a preselected volume of an electrolyte, 34. In this design, cathode 31 is a rotatable disk and anode 32 is a stationary cylinder. The cathode is positioned horizontally near the top of the level of electrolyte in container 33 and the anode is placed vertically of the container near its wall. An insulating cone, 35, which acts as a cdvc means, is positioned on the bottom of the container with a tip of the apex of the cone being at a distance G from the cathode. Current density across the cathode varies concentrically from a high at the edge of the cathode nearest the anode to a low at the center of the disc-cathode (nearest the apex of the insulating cone). Variation of the current density over the radius of the rotating disk can be obtained by varying the gap (G) between the disk and the tip (apex) of the cone-shaped insulator, the length of the anode (L) and the angle ($\Theta$) of the cone-shaped insulator.

Figure 4:
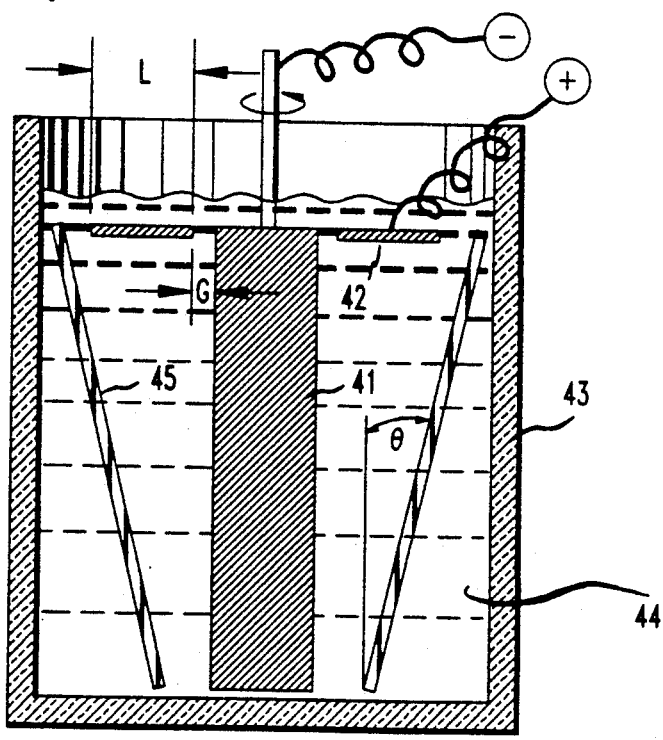
FIG. 4 is a schematic representation of a cell with a rotating cylinder cathode and a stationary washer-shape anode.

A still further embodiment of the invention, denominated 40, is schematically represented in FIG. 4 in which a cathode 41 and an anode 42 are positioned in a container 43 of non-conducting, non-contaminating material, holding an electrolyte, 44. In this design, cathode 41 is an elongated, narrow cylinder capable of being rotated about its longitudinal axis. Anode 42 is a stationary washer-shaped (annular) electrode. The cathode and the anode are positioned in the container with their longitudinal axes being substantially coaxial. An inverted, truncated insulating cone 45 positioned about the cylinder between the cylinder and the side walls of the container acts as a cdvc means. Current density across the cathode varies from a high at an upper end of the cylinder (nearest to the anode) to a low at a lower end of the cylinder. Adjustments in variation of the current density over the length of the cathode can be obtained by varying the gap (G) between the anode and the cathode, the radial length of the annular anode (L) and the angle (Θ) between the surface of the rotatable cylinder and the insulating object.

The feasibility of the improved cell was demonstrated using a cell of the first embodiment (FIG. 1) with a rotating cone-shaped cathode. The rotating cone was made of stainless steel. The base diameter of the cone was 9.5 cm, and the angle (Θ) of the cone was 32.5 degrees. The anode was a flat copper disk which had a diameter of 9.5 cm and was placed at the bottom of a 1000 ml container filled with 600 cc of a copper plating solution. The tip of the apex of the rotating cone was positioned 2.5 cm away of the anode, and the rotation of the cone was controlled at 100 rpm. The aqueous plating solution contained 20 g/l of copper sulfate and 160 g/l of sulfuric acid. Trace amount of commercially available copper plating additives were added. The total current applied to the cell was 2 Amps and plating time was approximately 80 minutes.

Figure 5:
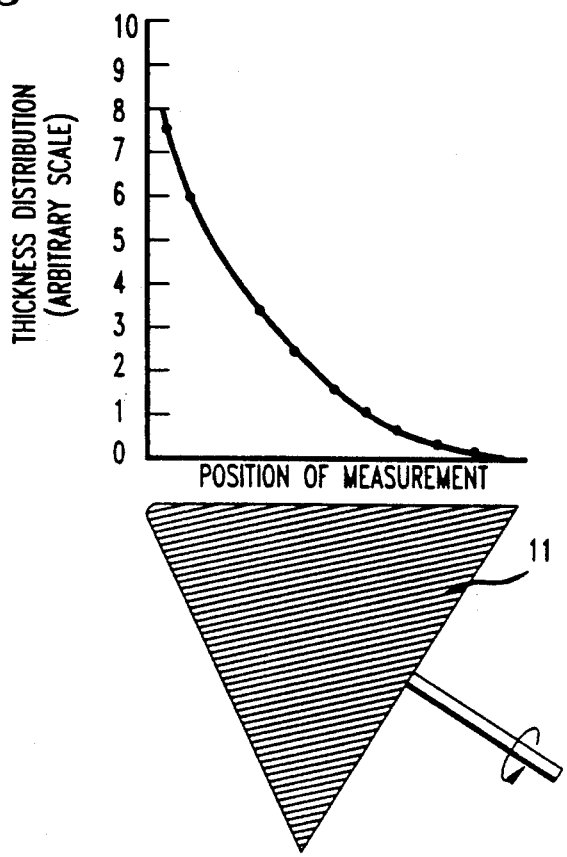
FIG. 5 is a plot of deposit thickness distribution on a rotating cone surface.
Figure 6:
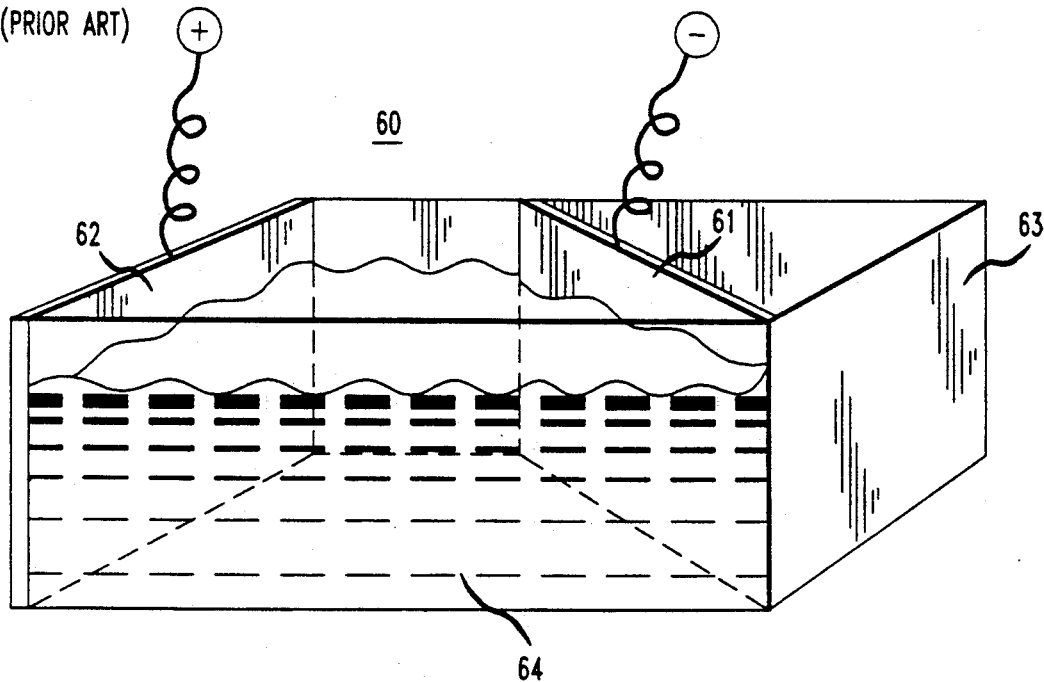
FIG. 6 is a schematic representation of the prior art, original Hull

In this instance the metal was plated directly onto the surface of the stainless steel cone, without the use of a test panel. After the electroplating, the copper deposit was peeled of the cone. A micrometer gage was used to measure the thickness of the copper deposit along the surface of the rotating cone. The thickness distribution of the deposit is plotted in FIG. 5 indicating, as in a Hull cell, a very wide achieved range of current densities.

To check the performance of reproducibility, three more experimental runs were performed. The total current applied to the cell was kept at 2 Amps, but the plating time was shortened to only 5 minutes to reduce additive concentration depletions during plating. Identical deposit appearances (dull and bright regions) were obtained for these three experimental runs. This demonstrates the reproducibility of the desired current variation. In addition, unlike a traditional Hull cell which usually showed some variations in appearance for the top and the bottom region of the test panel due to different mass transfer conditions, the rotating cone cell did not show any difference in appearance in the angular direction. The observations were not surprising due to the easiness of controlling the rotation speed, the well defined hydrodynamics, and the complete cell geometry symmetry. In addition, since the mass transfer conditions are extremely reproducible and can be easily modified by altering the rotation speed, the improved cell also can be used to study the mass transfer effect on deposit and throwing power.

I claim:

1. An improved electroplating cell comprising
   a container of non-conducting, non-contaminating material for holding electrolyte,
   an anode and a cathode positioned within the walls of the container, and
   a current density variation creating (cdvc) means of an electrically insulating material and for creating for a given total current a current density variation across the cathode, said cdvc means being arranged at an angle to that surface of the cathode on which deposition is to take place, said angle being less than 90 degrees,
   the volume of the electrolyte, when present, being sufficient for said anode, cathode and cdvc means being immersed in the electrolyte,
   wherein said anode and cathode are positioned coaxially each of another, and said cathode is capable of being rotated about its central axis.

2. The cell of claim 1, in which
   said anode is a flat disc positioned at the bottom of the container, and
   said cathode has a conical shape and is suspended above the anode, an apex of the cone facing the anode and being at a preselected distance from the anode,
   wherein an upright wall of the container acts as the said cdvc means.

3. The cell of claim 1, in which
   said anode has a cylindrical shape and is positioned within the walls of the container, coaxially thereof,
   said cathode has a conical shape and is suspended within a volume encircled by the anode and with an apex of the cone facing the bottom of the container, and
   the bottom of the container acts as the said cdvc means.

4. The cell of claim 1, in which
   said anode has a cylindrical shape and is positioned within the walls of the container coaxially thereof,
   said cathode is in the form of a disk positioned near the surface of the electrolyte in parallel to the bottom of the container, and
   said cdvc means is a cone of electrically insulating material protruding from the bottom of the container with an apex of the cone facing the cathode and being at a preselected distance from the cathode.

5. The cell of claim 1, in which
   said anode is in a form of an annulus positioned near the surface of the electrolyte in parallel to the bottom of the container,
   said cathode has a form of an elongated cylinder positioned coaxially of the anode, diameter of the cylinder being smaller than the central opening in the anode, and
   said cdvc means has a form of an inverted truncated cone positioned coaxially about the cathode and extending substantially the length of the cathode.

6. The cell of claim 1, in which
   said anode is also capable of being rotated about the central axis of the cathode.

* * * * *